(12) United States Patent
Karjalainen

(10) Patent No.: US 9,066,664 B2
(45) Date of Patent: Jun. 30, 2015

(54) DATA TRANSFER

(75) Inventor: Markku Karjalainen, Kempele (FI)

(73) Assignee: Polar Electro Oy, Kempele (FI)

( * ) Notice: Subject to any disclaimer, the term of this patent is extended or adjusted under 35 U.S.C. 154(b) by 0 days.

(21) Appl. No.: 13/202,796

(22) PCT Filed: Mar. 13, 2009

(86) PCT No.: PCT/FI2009/050198
§ 371 (c)(1),
(2), (4) Date: Aug. 24, 2011

(87) PCT Pub. No.: WO2010/103164
PCT Pub. Date: Sep. 16, 2010

(65) Prior Publication Data
US 2011/0313304 A1    Dec. 22, 2011

(51) Int. Cl.
*A61B 5/024* (2006.01)
*A61B 5/00* (2006.01)
*G06F 19/00* (2011.01)

(52) U.S. Cl.
CPC ........... *A61B 5/02438* (2013.01); *A61B 5/0006* (2013.01); *G06F 19/3418* (2013.01)

(58) Field of Classification Search
CPC .............. A61B 5/0006; A61B 5/02438; G06F 19/3418
USPC ................................................. 600/508, 509
See application file for complete search history.

(56) References Cited

U.S. PATENT DOCUMENTS

| | | | |
|---|---|---|---|
| 6,366,871 B1 | 4/2002 | Geva | |
| 6,540,663 B1 * | 4/2003 | Vau et al. | 600/27 |
| 2004/0266480 A1 * | 12/2004 | Hjelt et al. | 455/558 |
| 2005/0108055 A1 | 5/2005 | Ott et al. | |
| 2006/0220881 A1 * | 10/2006 | Al-Ali et al. | 340/573.1 |
| 2006/0224051 A1 * | 10/2006 | Teller et al. | 600/300 |
| 2006/0229523 A1 | 10/2006 | Barr | |
| 2006/0288147 A1 | 12/2006 | Hsieh | |
| 2007/0093719 A1 | 4/2007 | Nichols, Jr. et al. | |
| 2007/0142738 A1 * | 6/2007 | Hung | 600/519 |
| 2009/0018456 A1 * | 1/2009 | Hung | 600/509 |
| 2009/0037634 A1 * | 2/2009 | Kuris et al. | 710/303 |

FOREIGN PATENT DOCUMENTS

WO    98/30145 A1    7/1998

OTHER PUBLICATIONS

Tuomo Reiniaho, International Search Report for corresponding Finnish PCT Application, pp. 1-10 (Nov. 24, 2009).
Supplementary European Search Report for EP09841384, pp. 1-2 (Dec. 2, 2013).

* cited by examiner

*Primary Examiner* — Niketa Patel
*Assistant Examiner* — Lindsey G Hankins
(74) *Attorney, Agent, or Firm* — Hoffmann & Baron, LLP

(57) ABSTRACT

A data transfer component receives cardiac data from a heart sensor while the data transfer component is electromechanically coupled with the heart sensor sensitive to heart activity. A standard electromechanical interface of the data transfer component and a counterpart of the heart sensor are repeatedly connectable and disconnectable. The received data is stored in the data transfer component. The stored data is transferred from the data transfer component to an external device while the data transfer component is electromechanically coupled with the external device by using a coupling between the standard electromechanical interface of the data transfer component and a counterpart of the external device which are repeatedly connectable and disconnectable.

14 Claims, 5 Drawing Sheets

DATA TRANSFER

CROSS-REFERENCE TO RELATED APPLICATION

This application is a National Phase application of International Application No. PCT/FI2009/050198, filed Mar. 13, 2009, which is incorporated by reference herein in its entirety.

BACKGROUND

1. Field

The invention relates to data transfer in a user-specific portable heart rate monitor system.

2. Description of the Related Art

A user-specific portable heart rate monitor system typically comprises a user wearable structure such as a transmitter belt to be placed around the user's chest. The user wearable structure comprises an electronic circuit for detecting an electrocardiogram from the surface of the user's skin and for transmitting the electrocardiogram or a pulse characterizing a part thereof wirelessly to a user interface unit of the heart rate monitor, which typically is a wrist receiver to be placed on the user's wrist. The data on heart activity may be stored and processed in the user interface unit. The data may later be transferred from the user interface to an external computer for further processing.

The transmitting and storing of the data is complicated. Besides, wireless transmission is not always possible.

It is therefore useful to consider techniques that allow improvements in storing and transferring the measured data.

SUMMARY

An object of the invention is to provide improved data transfer. According to an aspect of the invention, there is provided a data transfer component for transferring cardiac data. The data transfer component comprises a heart sensor connector which is repeatedly connectable and disconnectable by an electromechanical coupling with a counterpart of a heart sensor that is capable of detecting heart activity of a person, wherein the data transfer component is configured to receive and store cardiac data on the heart activity while the heart sensor connector and the counterpart are coupled, the transfer component further comprising a standard electromechanical interface configured to communicate the cardiac data stored in the data transfer component to an external device, the standard electromechanical interface comprising the heart sensor connector.

The invention provides several advantages. The measured data can be stored during measurement and easily transferred to an external device.

BRIEF DESCRIPTION OF THE DRAWINGS

In the following, the invention will be described in greater detail by means of embodiments and the accompanying drawings, in which.

DETAILED DESCRIPTION

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments.

Figure 1:
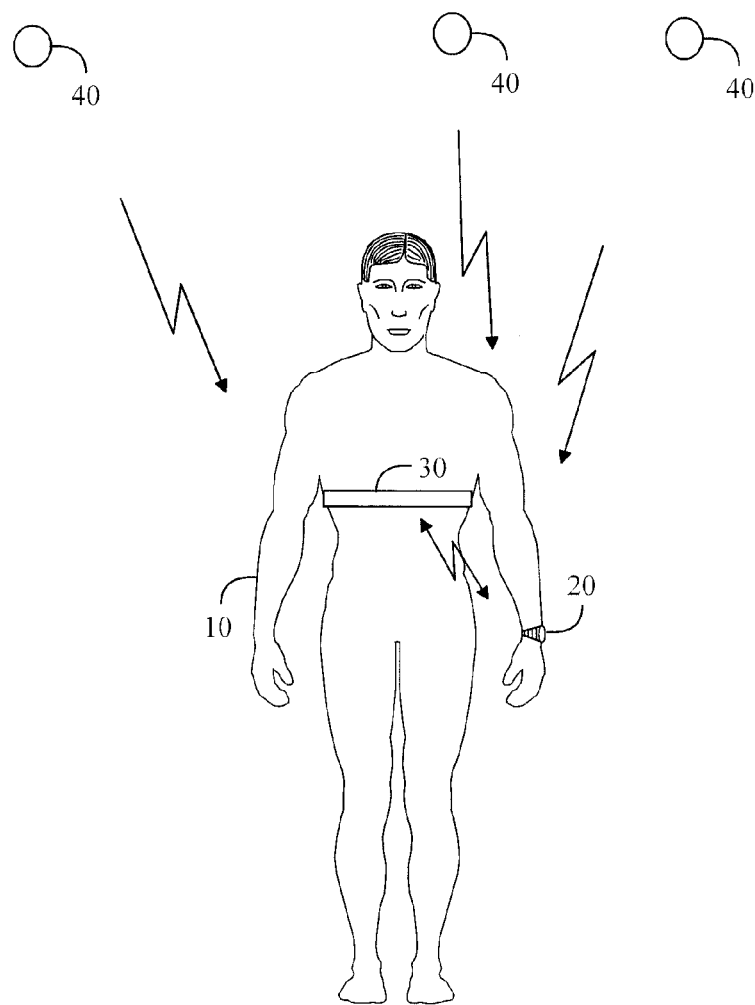
FIG. 1 shows a user-specific performance monitor system.

FIG. 1 presents a general concept of a portable user-specific performance monitor system such as a heart rate monitor. Polar Electro® designs and manufactures heart rate monitors and accessories for them. The user interface unit 20 may be a computer worn on the wrist, like a watch, but it may well be implemented on another kind of platform, such as a subscriber terminal of a radio system: a mobile telephone, for example. The user interface unit 20 may also be a sports watch for use as an instrument in sports. The user interface 20 may communicate with a user wearable structure 30. However, the user interface unit 20 is not necessarily needed in the present solution.

A data transfer component 100 and a heart sensor 106 (see FIGS. 2 to 11) may reside in the user wearable structure 30 which may be a belt worn around the chest of a person 10 using it. The user wearable structure 30 may also be a garment such as a shirt, an undervest, a top, a bra, or the like. The user wearable structure 30 may include metal or electrically conductive fabric electrodes in the heart sensor 106 for the electric contacts attachable to the person's skin. The fabric electrode may be, for example, felt, cloth, textile, or tissue. Electrodes 108 detect an electric signal that carries data on heart activity from the person's skin.

In an embodiment, the heart sensor 108 is based on an optical, acoustic or mechanical heart activity measurement.

In an embodiment, the user wearable structure 30 is a wrist strap.

In general, data includes a desirable piece of information and an irrelevant and/or undesirable piece of information. Cardiac data may include heart rate information, beat-to-beat intervals, and/or an electrocardiogram (ECG) as desirable information. Although cardiac data may be described using a frequency domain variable, i.e. the heart rate, in characterizing the cardiac data, the cardiac data may also be based on a time-domain approach, i.e., the heart beat intervals.

The wearable structure 30 may further comprise a supporting structure for supporting the data transfer component 100 so that the data transfer component 100 and the heart sensor 106 are reliably attached to each other during use.

Figure 2:
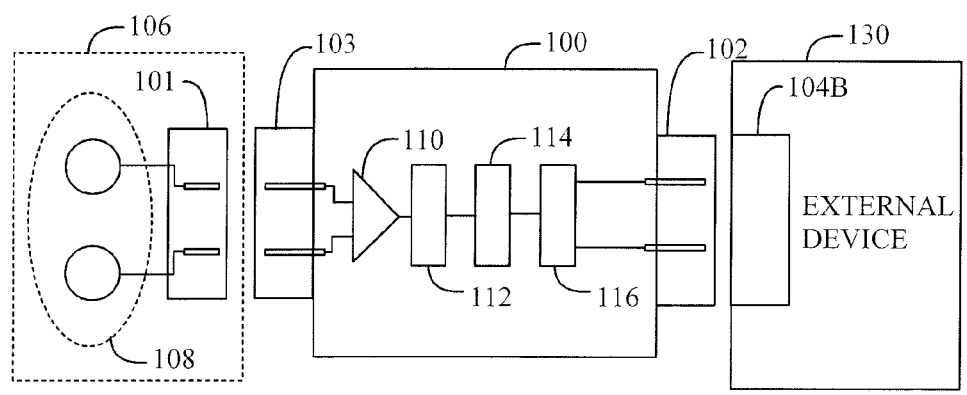
FIG. 2 illustrates a data transfer component, a heart sensor and their coupling elements.

FIG. 2 illustrates a data transfer component 100 and a heart sensor 106 in more detail. In an embodiment according to FIG. 2, the data transfer component 100 comprises a separate heart sensor connector 103 and a standard electromechanical interface 102.

The data transfer component 100 is typically small in size and easily transferable from a device to another.

In an embodiment of the invention, the data transfer component 100 comprises a waterproof plastic casing with an elongated structure. The external dimensions may be 3 to 10 mm (thickness), 10 to 20 mm (width), and 20 to 40 mm (length).

The heart sensor connector 103 is repeatedly connectable and disconnectable. The heart sensor connector 103 enables an electromechanical coupling with a counterpart 101 of the heart sensor 106. The heart sensor 106 may receive cardiac data on the heart activity of a person 10 when electrodes 108 are in contact with the person's skin. The data transfer component 100 may receive and store cardiac data while the heart sensor connector 103 and the counterpart 101 are coupled. Transferred cardiac data may include cardiac data on heart activity and/or some other data, such as user identification data, encryption data, and data associated with measurement variables.

An electromechanical coupling in this context comprises a galvanic connection between the heart sensor connector 103 and counterpart 101 of the heart sensor 106. The electromechanical coupling further comprises a mechanical coupling between the heart sensor connector 103 and the counterpart 101. The mechanical coupling may be implemented with a male-female-type coupling, for example. In an embodiment, common members are used for providing both the mechanical and electric coupling. In an embodiment, the electromechanical coupling is provided by press-studs.

In an embodiment, the electromechanical coupling also comprises an optical or inductive coupling.

In an embodiment, the data transfer component 100 comprises an amplifier 110 for amplifying signals carrying the cardiac data.

In an embodiment, the data transfer component 100 comprises an analog-to-digital converter 112 for converting a signal carrying the cardiac data from an analog form into a digital form.

In an embodiment, the data transfer component 100 comprises a controller 112 for processing the cardiac data. The processing may comprise controlling memory read/write operations, for example.

In an embodiment, the data transfer component 100 comprises a memory 116. The memory 116 may be a readable and writable mass memory implemented with a chip, for example. The memory 116 may comprise a flash memory, EEPROM (Electronically Erasable Programmable Read-Only Memory) and/or RAM (Random Access Memory).

In an embodiment, the data transfer component 100 comprises an amplifier 110, an analog-to-digital converter 112, a controller 114, and a memory 116. However, the distribution of these means between the data transfer component 100 and the heart sensor 106 may vary depending on the embodiment.

In an embodiment of the invention, the heart sensor 106 is detachably mountable to the user wearable structure 30, for example, by a press-stud or some other quick-disconnect fitting, but another type of fastening means may also be used. In such a case, both the heart sensor 106 and the data transfer component 100 may be detached and attached to the user wearable structure 30. The user wearable structure 30 may further comprise a supporting structure for supporting the data transfer component 100 so that the data transfer component 100 and the heart sensor 106 are reliably attached to each other and the user wearable structure 30 during use.

In an embodiment of the invention, the heart sensor 100 consists of electrodes 108 which are permanently fixed and/or integrated into the wearable structure 30. The data transfer component 100 may comprise an electromechanical instant coupling member, such as press-stud, for repeatedly connecting and disconnecting the data transfer component 100 with the counterpart 101 of the heart sensor 106.

The standard electromechanical interface 102 complies with a standard mechanical structure, pin order, pin function, and possibly a data transfer protocol. The standard electromechanical interface 102 may comply with the following standardized bus types: a generation of a USB (Universal Serial Bus) port, such as USB A, USB B, mini-USB, and/or a HDMI (High Definition Multimedia interface).

In an embodiment, the user wearable structure 30 may comprise a transmitter 500, 502 transmitting electromagnetic radiation or magnetic pulses carrying cardiac data.

In an embodiment, the user wearable structure 30 receives data from satellites 40 for determining its global position.

A counterpart 104B to the standard electromechanical interface 102 of the data transfer component 100 is repeatedly connectable and disconnectable. The counterpart 104A enables an electromechanical coupling with the standard electromechanical interface 102 of the data transfer component 100 for transferring the cardiac data to an external device 130.

With reference to FIGS. 3 to 10, illustrates embodiments in which the standard electromechanical interface 102 comprises the heart sensor connector 103. This results in that the standard electromechanical interface 102 enables coupling the data transfer component 100 both with the heart sensor 106 and the external device 130. This embodiment simplifies the structure of the data transfer component 100, since the number of wired interface s is reduced. In this case, a counterpart 104A of the heart sensor 106 is mechanically and electrically compatible with the standard electromechanical interface 102. The compatibility in this context means that the counterpart 104A of the heart sensor 106 is mechanically and electrically connectable to and disconnectable from the standard electromechanical interface 102. However, as the functionality of the connection between the standard electromechanical interface 102 and the counterpart 104 may differ from the functionality defined by the standard, the pin order, pin functionality and/or data transfer protocol may deviate from that defined in the standard of the standard electromechanical interface 102. The pin functionality in this context means the use of the pin for transfer of analog signals, digital signals, or power. The pin functionality may also comprise the signal level of signals conducted by the pins.

In an embodiment of the invention, the electromechanical standard interface 102 also comprises an optical and/or inductive coupling.

In an embodiment of the invention, the data transfer component 100 comprises a multiplexer 118 coupled with the standard electromechanical interface 102. The multiplexer 118 comprises a circuitry and possibly a control logic to change the operation mode of the standard electromechanical interface 102 according to whether the data transfer component is coupled with the heart sensor 100 or with the external device 600.

The multiplexer 118 may be connected to the controller 114 which inputs data and possibly control bits into the multiplexer 118. The multiplexer 118 directs the data to the desired pins, ports, or poles of the standard electromechanical interface 102.

Operation modes include a configuration of pin functionalities. For example, in a first operation mode, the pins of the standard electromechanical interface 102 are used as defined in the standard. In this case, the first operation mode is used for coupling the data transfer component 100 with an external device, such as a computer or a mobile phone supporting the standard of the standard electromechanical interface 102. In a second operation mode, the pins may be used freely according to the specification defined for signal transfer between the heart sensor 106 and the data transfer component 100. The specification may specify that a digital bus according to the standard is used for transferring analog signals or power, for example.

Figure 3:
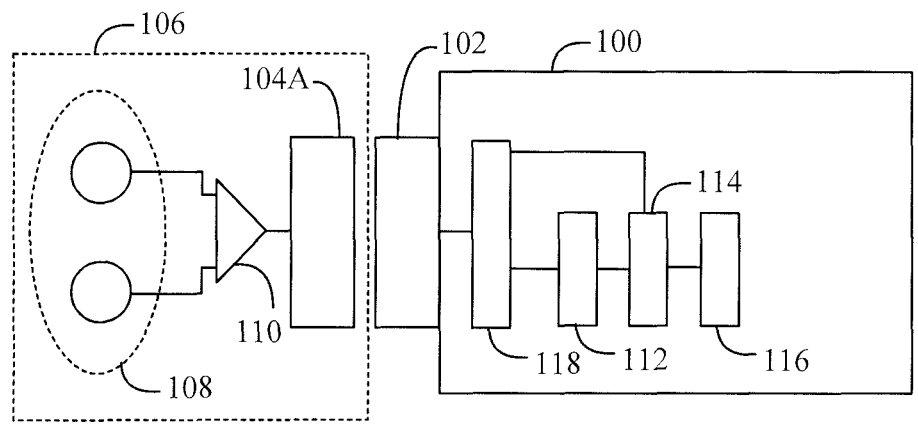
FIG. 3 illustrates a second distribution of operational elements between the data transfer component and the heart sensor.

FIG. 3 presents an embodiment where the heart sensor 106 comprises electrodes 108, a counterpart 104A, and an amplifier 110. In this embodiment, the data transfer component 100 comprises an analog-to-digital converter 112, a controller 114 and a memory 116. In this embodiment, the cardiac data is transferred in an analog form from the heart sensor 106 to the data transfer component. The analog-to-digital converter 112 converts an amplified signal carrying the cardiac data into a digital form and feeds a digital signal into the controller 114. The controller 114 processes the digital signal, and feeds a processed data or raw digital cardiac data into the memory 116.

Figure 4:
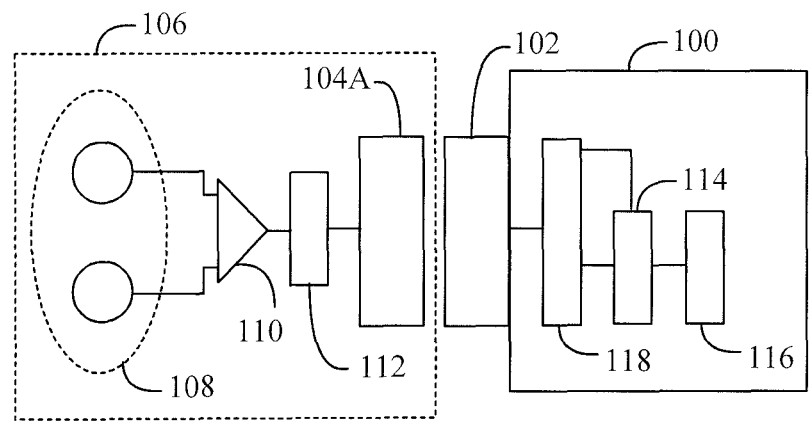
FIG. 4 illustrates a third distribution of operational elements between the data transfer component and the heart sensor.

FIG. 4 presents an embodiment where the heart sensor 106 comprises electrodes 108, a counterpart 104A, an amplifier 110, and an analog-digital converter 112. The data transfer component 100 may then comprise a controller 114 and a memory 116. The functions of the amplifier 110, analog-to-digital converter 112, the controller 114, and the memory 116 are similar to those described in conjunction with FIG. 3. In this embodiment, the cardiac data is inputted in a digital form from the heart sensor 106 into the data transfer component 100. In this embodiment, the transfer of the cardiac data from the heart sensor 106 to the data transfer component 100 is more reliable.

Figure 5:
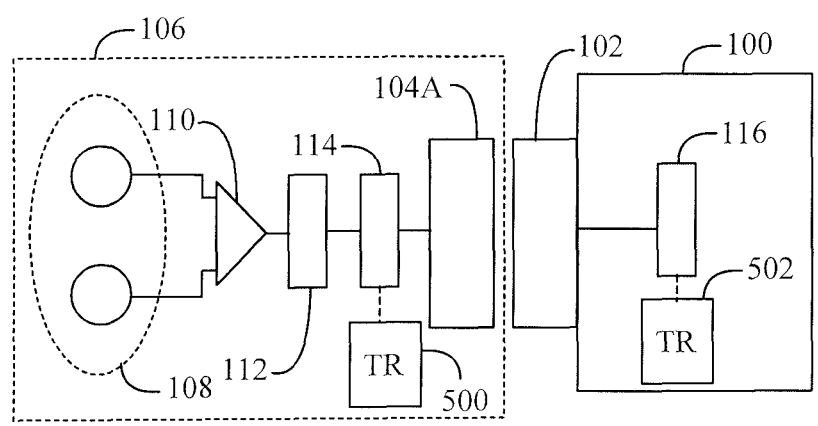
FIG. 5 illustrates a fourth distribution of operational elements between the data transfer component and the heart sensor.

FIG. 5 presents an embodiment where the heart sensor 106 comprises electrodes 108, a counterpart 104A, an amplifier 110, an analog-to-digital converter 112, and a controller 114. The data transfer component 100 may then comprise a memory 116. The functions of the amplifier 110, analog-to-digital converter 112, the controller 114 and the memory 116 are similar to those described in conjunction with FIG. 3. This embodiment enables a simplified structure for the data transfer component 100.

The heart sensor 106 may also comprise a wireless transmitter 500 which may transmit the data on the activity of the heart to the user interface 20 or to some other device.

Alternatively or additionally, the data transfer component 100 may comprise a wireless transmitter 502 which may transmit the data on the activity of the heart to the user interface 20 or to some other device.

The transmitters 500, 502 may transmit electromagnetic radiation or magnetic pulses carrying the cardiac data. The frequency of the magnetic pulses may be about 5 kH and the carrier frequency of the electromagnetic radiation may be about 2.4-gigahertz, for example. The magnetic pulses may be transmitted and received using a coil as an antenna.

In FIGS. 2 to 5, the controller 114, which may be a processor or a combinational logic circuit, is not necessarily needed and the digital data from the analog-to-digital converter 112 may be directly be transferred to the memory 116.

Figure 6:
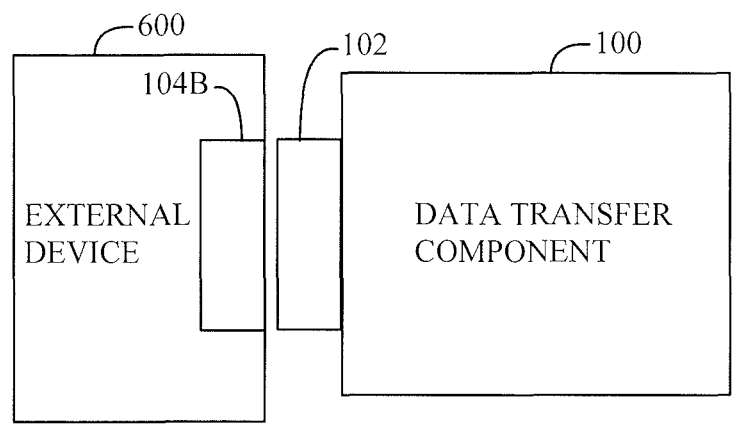
FIG. 6 illustrates a coupling between the data transfer component and the heart sensor.

According to the embodiment shown in FIG. 6, the standard electromechanical interface 102 also enables an electromechanical coupling with a counterpart 104B of an external device 600 for transferring the data stored in the data transfer component 100 to the external device 600. The external device 600 may be a computer or a mobile phone which may process and present results based on the data transferred to it.

The electrical coupling between the standard electromechanical interface 102 and the counterpart 104A or 104B may be galvanic such that electrically conductive materials are in a physical contact with each other.

Figure 7:
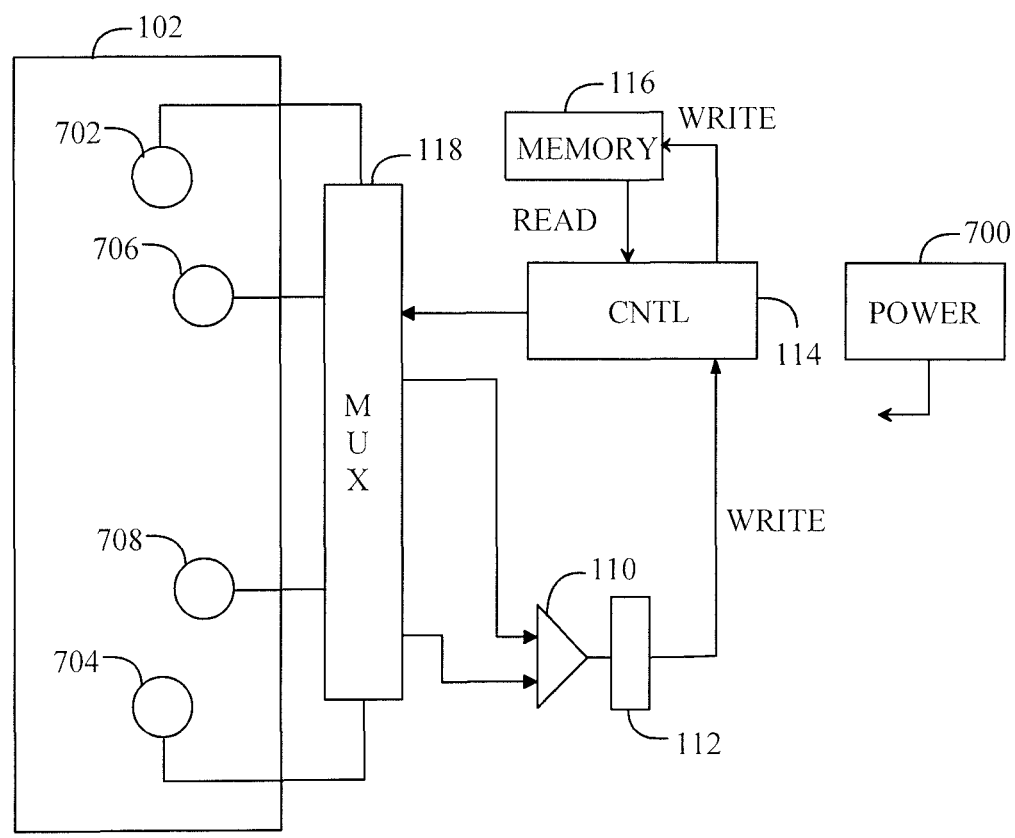
FIG. 7 illustrates a detection automaton for receiving electric power to the data transfer component.

FIG. 7 presents an embodiment where the data transfer component 100 comprises an amplifier 110, an analog-to-digital converter 112, a controller 114, and a memory 116. The data transfer component 100 may also comprise an electric power source 700 for energizing the operation of the data transfer component 100. The controller's 114 function may in this case be as simple as multiplexing. The standard electromechanical interface 102 may comprise poles 702, 704, also referred to as pins or the like, for the reception of operation power. The standard electromechanical interface 102 may also comprise poles 706, 708 for inputting or outputting data. When the controller 114 detects that a coupling can provide the poles 702, 704 with appropriate electric power, the power source 700 of the data transfer component 100 may be disconnected from use. When the controller 114 detects that a coupling cannot provide the poles 702, 704 with appropriate electric power, the power source 700 of the data transfer component 100 is used for the operation of the data transfer component 100. The coupling of poles may be controlled by the controller 114 and implemented by the multiplexer 118.

For example, when the data transfer component is coupled with the heart sensor 106, the heart sensor 106 may only feed an unprocessed analog data signal to the poles 706, 708 of the standard electromechanical interface 102 but have no electric power feed to the poles 702, 704. The data transfer component 100 then uses its own power source 700 for its own operation. Additionally, the controller 114 of the data transfer component 100 may switch on the coupling from the input data from poles 706, 708 through the amplifier 110 and the analog-to-digital converter 112 to the memory 116.

Figure 8:
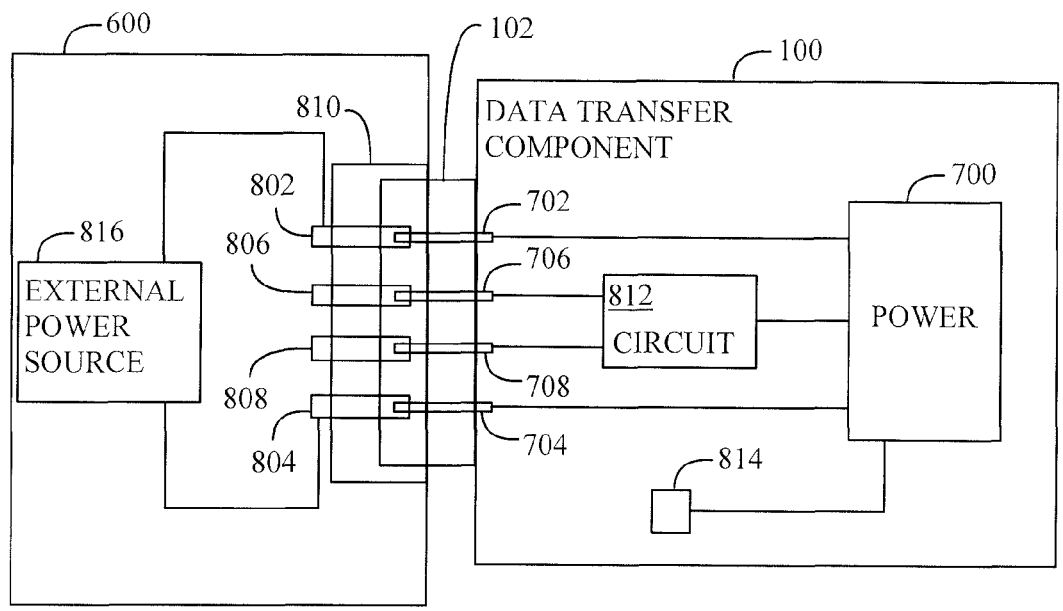
FIG. 8 illustrates charging of the power source in the data transfer component.

As to FIG. 8, let us assume now that the external device 600 has its own electric power source. When the data transfer component 100 is coupled with the external device 600, the poles 802, 804 of the counterpart 810 of the external device 600 may feed appropriate electric power to the poles 702, 704 of the standard electromechanical interface 102 of the data transfer component 100. The controller 114 may then receive electric power for its operation from the external device 600. The controller 114 may also let the memory 116 in a circuit 812 output data to the poles 706, 708 of the standard electromechanical interface 102. The poles 806, 808 of the external device 600 may then receive the output data so that the external device 600 may read the data.

The circuit 812 comprises at least the memory 116 but may additionally comprise at least one of the following: the amplifier 110, the multiplexer 118, the analog-to-digital converter 112, and the controller 114. The electric circuit 812 may comprise logic components, standard integrated circuits, application-specific integrated circuits (ASIC), and/or other suitable electronic circuits.

In an embodiment, the memory 116 of the data transfer component 100 may include at least one driver program. A driver program is a computer program that enables the data transfer component 100 to start, continue and end communication with the external device 600. Additionally, address data may have been stored in the memory 116 such that the driver program in the data transfer component 100 may use the address data to transfer data, such as data on heart activity, from the data transfer component 100 to at least one specific address in the external device 600.

In an embodiment, the memory 116 comprises a computer program which automatically connects, when executed in the external device 600, the data transfer component to a desired address which may be a computer address or an Internet address. Furthermore, the memory 116 may further comprise a computer program which automatically, when executed in the external device 600, transmits the cardiac data or part thereof to a desired address which may be a computer address or an Internet address.

In an embodiment, the controller 114 may include a ciphering program to encrypt data fed into the memory 116 of the data transfer component 100. The ciphering program may also decipher the enciphered data. The data may be transferred from the data transfer component 100 in a ciphered or in a deciphered form. Ciphering may be needed in applications, where the user is not allowed to interfere or manipulate the cardiac data.

In an embodiment, a controller comprises a program or an algorithm to form user authentication data on the basis of the cardiac data and incorporate the user authentication data into the cardiac data. User authentication may be needed in cases where there is a risk of associating the data with wrong user. The user authentication may be based on ECG recording and storage, for example. In an embodiment of the invention, the controller records the user's ECG at predetermined time intervals and codes the ECG data into the cardiac data.

FIG. 8 also shows charging. In this embodiment, the external device 600 may be a charger feeding electric charging power through the coupling of the standard electromechanical interface 102 and its counterpart 810 to the power source 700 of the data transfer component 100. The counterpart 810 is similar to the counterpart 104A, 104B. The data transfer component 100 may comprise an indicator 814 which may indicate to a user that the power source 700 is being charged. The indicator 814 may have an acoustic source and/or visible light source. The light source 814 may, for example, radiate red light when the power source 700 is being charged. When the power source 700 reaches the maximum charge, the light may turn green to indicate that the data transfer component 100 may be disconnected from the external device 600. Additionally or alternatively, the indicator 814 may generate an acoustic signal to be heard when the power source 700 becomes fully charged.

The indicator 814 may also comprise a display capable of presenting alphanumeric and/or graphic information on the operational state of the data transfer component 100 and/or the charging state of the power source 700.

Figure 9:
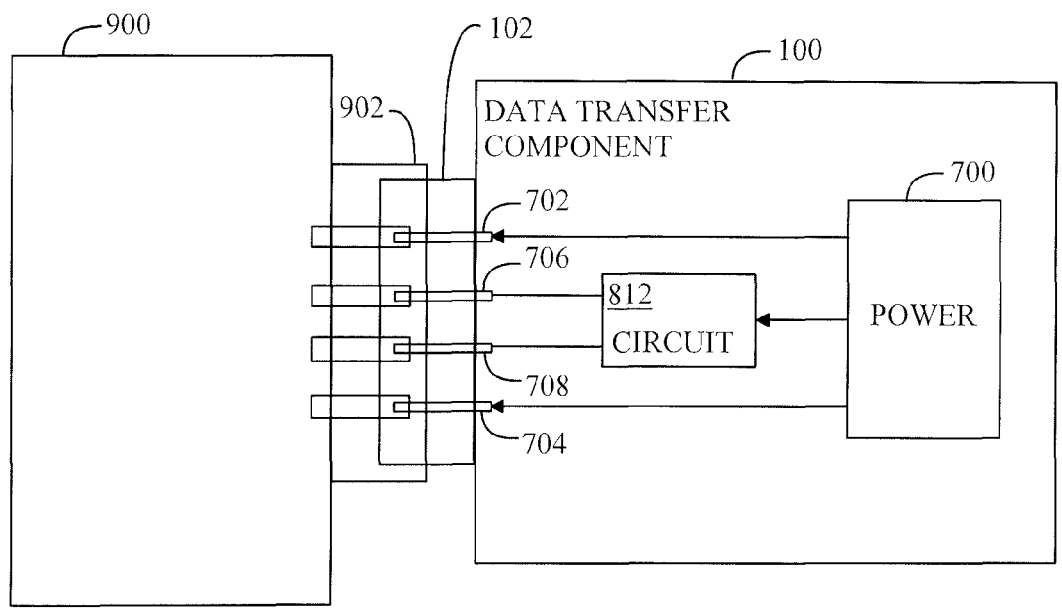
FIG. 9 illustrates an embodiment where the data transfer component feeds electric power to a separate device through the coupling therebetween.

FIG. 9 presents an embodiment where the data transfer component 100 is coupled with a device 900. The electric power source 700 of the data transfer component 100 may feed electric power to the device 900 through the coupling of the standard electromechanical interface 102 and its counterpart 902 of the device 900 which may be the heart sensor 106 or an external device 600. Thus, the counterpart 902 may be the counterpart 104A or 104B. In this way, the heart sensor 106 may receive electric power for its operation from the data transfer component 100 through the coupling of the standard electromechanical interface 102 and the counterpart 104A. The electric power source 700 may also feed the circuit 812 of the data transfer component 100.

Figure 10:
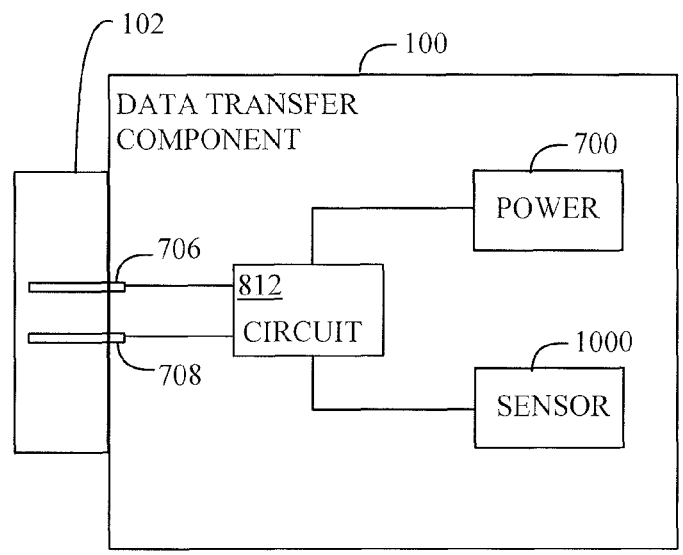
FIG. 10 illustrates the data transfer component with an additional sensor.

FIG. 10 presents an embodiment where the data transfer component 100 comprises at least one additional sensor 1000 which may measure a measurable variable which is different from that provided by the heart sensor 106. Alternatively, the additional sensor 1000 may reside in the heart sensor 106. The additional sensor 1000 may feed its data to the circuit 812 of the data transfer component 100 to be processed and/or stored.

In an embodiment, the additional sensor 1000 may be an environment sensor such as a resistive sensor, capacitive sensor, altimeter, hygrometer or the like which measures a variable relating to the environment. The environment sensor may determine whether the person 10 is in water, for example, swimming or diving because the measured resistance and/or the capacitance between the electrodes of the environment sensor is different in air than in water. Let us assume that the data transfer component 100 or the heart sensor 106 is capable of transmitting wirelessly. If the environment sensor now detects that the person 10 is in water, the controller 114 may switch the wireless transmission of data off and control the memory 116 to store the data on heart activity. After the environment sensor detects that the person 10 is not in water, the wireless transmission may continue.

In an embodiment, the environmental sensor may be a hygrometer. If the humidity measured by the hygrometer exceeds a predefined threshold, which may for instance be the highest humidity value of the hygrometer (for air) or some other suitable value, it can be assumed that the hygrometer is in water, which means that wireless data transmission is not available. The hygrometer may measure and form data on humidity which may be stored in the memory 116.

If the environmental sensor is an altimeter, it may measure and form data on the altitude at which the person 10 is. The measurement is often made as an air pressure measurement. Because the density of water, for instance, is higher than that of air, pressure measurement can also be used to detect the movement of the person 10 from air to water and vice versa. The altimeter may measure and form data on altitude which may be stored in the memory 116.

In an embodiment, the additional sensor 1000 may be a receiver for receiving positioning data from satellites 40 of a satellite positioning system. In this case, the measurement variable is location and/or speed. The positioning data from the satellites 40 of a satellite positioning system is vector data on the position of a person 10 and the vector data may come from the satellites 40 of a satellite positioning system directly or indirectly via a separate satellite positioning sensor. The satellite positioning system may be based on GPS (Global Positioning System), GLONASS (Global Navigation Satellite System), Galileo (Galileo positioning system), Beidou Navigation System, (IRNSS) Indian Regional Navigational Satellite System, or the like. The vector data may define the position of the receiver (associated with the person) of the satellite signals three dimensionally (3D), two dimensionally (2D) or one dimensionally (1D) based on longitude, latitude and/or altitude. Additionally or alternatively, the additional sensor 1000 may determine its position utilizing other known positioning techniques. In an embodiment, the additional sensor 1000 receives radio signals from at least one base station of a radio system, determines the position of the at least one base station and timing of the signals, and determines its position on the basis of the position of the at least one base station and the determined timing.

When the determined position is changing, the controller 114 may form the speed of the person 10 on the basis of the measured distance and time.

In an embodiment, the additional sensor 1000 may be an acceleration sensor. When the person 10 is running or walking he/she experiences acceleration variation which can be measured inertially by an acceleration sensor sensitive to the inertial forces. An inertial algorithm, which may be performed in the controller 114 or in the external device 600, may form data on acceleration, speed and/or traveled distance of the person 10.

The measured data on a position, acceleration and/or a speed may be stored in the memory 116.

In an embodiment, the additional sensor 1000 may be a thermometer for measuring and forming data on temperature of the person 10 or the environment, and the temperature data may be stored in the memory 116.

In an embodiment, the additional sensor 1000 may be a magnetic sensor which measures the magnetic field of the earth. For example, when the person 10 swims in a pool back and forth, the change of direction of the magnetic field is 180°, when the person 10 turns from one direction to the opposite direction. The time between two changes of direction indicates how long it takes for the person 10 to swim from one end of the pool to the other. This way it is possible to measure the swimming time and distance, if the length of the pool is known. The measured data on a distance and/or strength of the magnetic field may be stored in the memory 116.

In an embodiment, the additional sensor 1000 may be a strain gauge which may measure a resistance or a capacitance. In the strain gauge, the resistance or the capacitance of the gauge depends on the changing geometry of the sensor. For example, when the belt around the chest of the person 10 stretches and contracts due to breathing, data on the frequency and the depth of breathing may be detected. The measured data on breathing may be stored in the memory 116.

Figure 11:
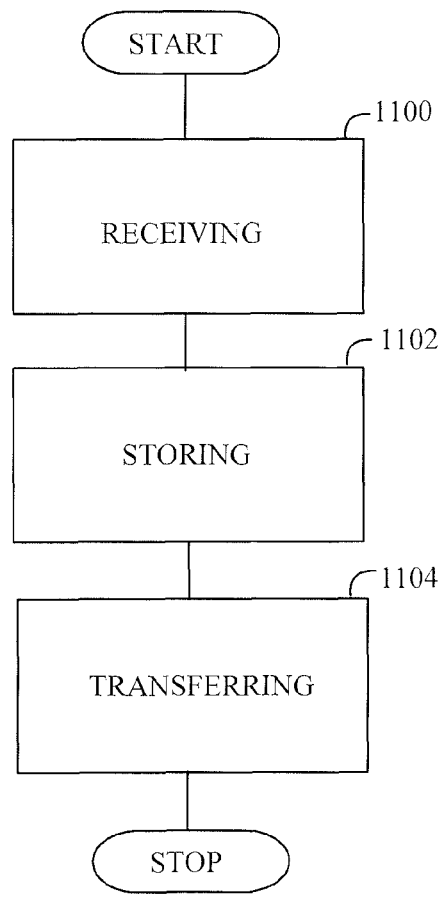
FIG. 11 presents a flow chart of a method.

FIG. 11 presents a flow chart of a data transfer method. In step 1100, data on heart activity is received by a data transfer component 100 from a heart sensor 106 while the data transfer component 100 is electromechanically coupled with the heart sensor 106 sensitive to heart activity by using a coupling between a standard electromechanical interface 102 of the data transfer component 100 and the counterpart 104A of the heart sensor 106, which are repeatedly connectable and disconnectable. In step 1102, the received data is stored in the data transfer component 100. In step 1104, the stored data is transferred from the data transfer component 100 to an external device 600 while the data transfer component 100 is electromechanically coupled with the external device 600 by using a coupling between the standard electromechanical interface 102 of the data transfer component 100 and the counterpart 104B of the external device 600, which are repeatedly connectable and disconnectable.

The controller 114 may be configured to control the performance of at least some of the steps described in connection with the flowchart of FIG. 11. The embodiments may be implemented as a computer program comprising instructions for executing a computer process for the data transfer.

The controller 114 may be a microprocessor which implements functions of a central processing unit (CPU) on an integrated circuit. The CPU is a logic machine executing a computer program which comprises program instructions. The program instructions may be coded as a computer program using a programming language, which may be a high-level programming language, such as C, or Java, or a low-level programming language, such as a machine language, or an assembler. The CPU may comprise a set of registers, an arithmetic logic unit (ALU), and a control unit. The control unit is controlled by a sequence of program instructions transferred to the CPU from a program memory. The control unit may contain a number of microinstructions for basic operations. The implementation of the microinstructions may vary depending on the CPU design. The microprocessor may also have an operating system (a dedicated operating system of an embedded system, or a realtime operating system), which may provide system services to the computer program. The controller 114 may include a clock for measuring time.

The computer program may be stored on a computer program distribution medium readable by a computer or a processor. The computer program medium may be, for example but not limited to, an electric, magnetic, optical, infrared or semiconductor system, device or transmission medium. The computer program medium may include at least one of the following media: a computer readable medium, a program storage medium, a record medium, a computer readable memory, a random access memory, an erasable programmable read-only memory, a computer readable software distribution package, a computer readable signal, a computer readable telecommunications signal, computer readable printed matter, and a computer readable compressed software package.

Even though the invention has been described above with reference to an example according to the accompanying drawings, it is clear that the invention is not restricted thereto but can be modified in several ways within the scope of the appended claims.

What is claimed is:

1. A data transfer component for transferring cardiac data, the data transfer component comprising:
a heart sensor connector which is configured to be repeatedly connected and disconnected by an electromechanical coupling with a counterpart of a heart sensor detecting heart activity of a person, wherein the data transfer component is configured to receive and store cardiac data representing the heart activity while the heart sensor connector and the counterpart of the heart rate sensor are coupled; and
a standard electromechanical interface configured to communicate the cardiac data stored in the data transfer component to an external device, the standard electromechanical interface comprising the heart sensor connector and configured to be repeatedly connected and disconnected to the external device by the electromechanical coupling, the standard electromechanical interface coupling the data transfer component with either the counterpart of the heart sensor, thereby enabling reception and storage of the cardiac data using the heart sensor connector, or to the external device, thereby enabling communication of the cardiac data to the external device using the heart sensor connector, wherein the data transfer component comprises a multiplexer coupled with the standard electromechanical interface, wherein the multiplexer reconfigures connections associated with the standard electromechanical interface in response to whether the data transfer component is coupled with the heart sensor or with the external device.

2. The data transfer component of claim 1, wherein the data transfer component comprises an electric power source configured to energize the operation of the data transfer component.

3. The data transfer component of claim 2, wherein the standard electromechanical interface is configured to enable an electromechanical coupling with a counterpart of an external power source for charging the electric power source of the data transfer component.

4. A data transfer component for transferring cardiac data, the data transfer component comprising:
a heart sensor connector which is configured to be repeatedly connected and disconnected by an electromechanical coupling with a counterpart of a heart sensor detecting heart activity of a person, wherein the data transfer component is configured to receive and store cardiac data representing the heart activity while the heart sensor connector and the counterpart of the heart rate sensor are coupled; and a standard electromechanical interface configured to communicate the cardiac data stored in the data transfer component to an external device, the standard electromechanical interface comprising the heart sensor connector and configured to be repeatedly connected and disconnected to the external device by the electromechanical coupling, the standard electromechanical interface coupling the data transfer component with either the counterpart of the heart sensor, thereby enabling reception and storage of the cardiac data using the heart sensor connector, or to the external device, thereby enabling communication of the cardiac data to the external device using the heart sensor connector, wherein the data transfer component comprises an electric power source configured to energize the operation of the data transfer component, wherein the electric power source feeds electric power through the heart sensor connector to the counterpart of the heart sensor coupled with it.

5. A data transfer component for transferring cardiac data, the data transfer component comprising:

a heart sensor connector which is configured to be repeatedly connected and disconnected by an electromechanical coupling with a counterpart of a heart sensor detecting heart activity of a person, wherein the data transfer component is configured to receive and store cardiac data representing the heart activity while the heart sensor connector and the counterpart of the heart rate sensor are coupled; and a standard electromechanical interface configured to communicate the cardiac data stored in the data transfer component to an external device, the standard electromechanical interface comprising the heart sensor connector and configured to be repeatedly connected and disconnected to the external device by the electromechanical coupling, the standard electromechanical interface coupling the data transfer component with either the counterpart of the heart sensor, thereby enabling reception and storage of the cardiac data using the heart sensor connector, or to the external device, thereby enabling communication of the cardiac data to the external device using the heart sensor connector, wherein the data transfer component comprises at least one additional sensor that measures a measurable variable different from that provided by the heart sensor, and the data transfer component stores data on the measurable variable.

6. The data transfer component of claim 1, wherein the data transfer component further comprises an amplifier for amplifying signals carrying the cardiac data.

7. The data transfer component of claim 1, wherein the data transfer component further comprises an analog-to-digital converter for converting a signal carrying the cardiac data from an analog form into a digital form.

8. The data transfer component of claim 1, wherein the data transfer component further comprises a controller for processing the cardiac data.

9. The data transfer component of claim 8, wherein the controller encrypts the cardiac data.

10. A data transfer component for transferring cardiac data, the data transfer component comprising:

a heart sensor connector which is configured to be repeatedly connected and disconnected by an electromechanical coupling with a counterpart of a heart sensor detecting heart activity of a person, wherein the data transfer component is configured to receive and store cardiac data representing the heart activity while the heart sensor connector and the counterpart of the heart rate sensor are coupled; and a standard electromechanical interface configured to communicate the cardiac data stored in the data transfer component to an external device, the standard electromechanical interface comprising the heart sensor connector and configured to be repeatedly connected and disconnected to the external device by the electromechanical coupling, the standard electromechanical interface coupling the data transfer component with either the counterpart of the heart sensor, thereby enabling reception and storage of the cardiac data using the heart sensor connector, or to the external device, thereby enabling communication of the cardiac data to the external device using the heart sensor connector, wherein the data transfer component further comprises a controller for processing the cardiac data, wherein the controller forms user authentication data on the basis of the cardiac data and incorporates the user authentication data into the cardiac data.

11. The data transfer component of claim 1, wherein the counterpart of the heart sensor is further coupled to at least one additional sensor configured to measure a measurable variable different from that provided by the heart sensor, and the data transfer component is further configured to receive and store data on the measurable variable from the at least one additional sensor while the heart sensor connector and the counterpart are coupled.

12. The data transfer component of claim 11, wherein the at least one additional sensor comprises at least one of a resistive sensor, a capacitive sensor, an altimeter, a hygrometer for measuring a variable relating to surrounding environmental conditions, a receiver for receiving satellite positioning data, an accelerometer, and a magnetic sensor.

13. The data transfer component of claim 5, wherein the at least one additional sensor comprises at least one of a resistive sensor, a capacitive sensor, an altimeter, a hygrometer for measuring a variable relating to surrounding environmental conditions, a receiver for receiving satellite positioning data, an accelerometer, and a magnetic sensor.

14. The data transfer component of claim 1, wherein the standard electromechanical interface comprises two poles for reception of operational power and two poles for receiving and storing cardiac data while the heart sensor connector and the counterpart are coupled and for communicating the cardiac data stored in the data transfer component to an external device while the heart sensor connector is coupled to the external device.

* * * * *